United States Patent
Seen

(10) Patent No.: US 10,602,994 B2
(45) Date of Patent: Mar. 31, 2020

(54) X-RAY TABLE AND X-RAY SYSTEM COMPRISING SAME

(71) Applicant: Dong June Seen, Gimpo-si (KR)

(72) Inventor: Dong June Seen, Gimpo-si (KR)

(*) Notice: Subject to any disclaimer, the term of this patent is extended or adjusted under 35 U.S.C. 154(b) by 337 days.

(21) Appl. No.: 15/501,440

(22) PCT Filed: Aug. 5, 2015

(86) PCT No.: PCT/KR2015/008183
§ 371 (c)(1),
(2) Date: Feb. 3, 2017

(87) PCT Pub. No.: WO2016/021931
PCT Pub. Date: Feb. 11, 2016

(65) Prior Publication Data
US 2017/0215819 A1  Aug. 3, 2017

(30) Foreign Application Priority Data

Aug. 6, 2014 (KR) .................. 10-2014-0100916
Sep. 3, 2014 (KR) .................. 10-2014-0117235
Sep. 22, 2014 (KR) .................. 10-2014-0126237

(51) Int. Cl.
*A61B 6/04* (2006.01)
*A61B 6/00* (2006.01)
*A61G 13/04* (2006.01)
*A61G 13/00* (2006.01)

(52) U.S. Cl.
CPC .............. *A61B 6/0407* (2013.01); *A61B 6/00* (2013.01); *A61B 6/04* (2013.01); *A61B 6/0421* (2013.01); *A61B 6/4464* (2013.01); *A61G 13/00* (2013.01); *A61G 13/04* (2013.01)

(58) Field of Classification Search
CPC .......... A61B 6/0407; A61B 6/00; A61B 6/04; A61B 6/0421; A61B 6/4464; A61B 13/04; A61G 13/00
USPC .......................................................... 378/209
See application file for complete search history.

(56) References Cited

U.S. PATENT DOCUMENTS 2,680,046 A * 6/1954 Stava .................. A61B 6/04
  108/2
2,692,173 A * 10/1954 Lowitzsch ............ A61B 6/04
  108/2
3,131,301 A * 4/1964 Barrett ................ A61B 6/04
  108/2
3,525,308 A * 8/1970 Koopmans ............ A61B 6/04
  108/8

(Continued)

FOREIGN PATENT DOCUMENTS

JP       2005-204857 A      8/2005
KR   20-2008-0001159 U      5/2008

(Continued)

OTHER PUBLICATIONS

International Search Report in International Application No. PCT/KR2015/008183, dated Dec. 11, 2015.

*Primary Examiner* — Nicholas F Polito
*Assistant Examiner* — Rahib T Zaman
(74) *Attorney, Agent, or Firm* — Park, Kim & Suh, LLC

(57) ABSTRACT

An X-ray table and an X-ray system including the X-ray table are provided. The X-ray table can reversibly rotate without interfering with an X-ray imaging unit while a top surface thereof faces the X-ray imaging unit.

16 Claims, 9 Drawing Sheets

(56) References Cited

U.S. PATENT DOCUMENTS

| | | | | |
|---|---|---|---|---|
| 3,532,882 A | * | 10/1970 | Craig | A61B 6/04 378/209 |
| 4,618,133 A | * | 10/1986 | Siczek | A61B 6/447 378/209 |
| 4,697,802 A | | 10/1987 | Brendl et al. | |
| 4,841,585 A | * | 6/1989 | Masuzawa | A47C 19/045 378/209 |
| 5,014,292 A | * | 5/1991 | Siczek | A61B 6/00 378/195 |
| 5,155,758 A | * | 10/1992 | Vogl | A61B 6/04 378/208 |
| 5,655,238 A | * | 8/1997 | Stickley | A61G 13/04 5/618 |
| 5,790,996 A | * | 8/1998 | Narfstrom | A61G 13/04 108/6 |
| 5,829,076 A | * | 11/1998 | Csikos | A61B 6/0457 5/601 |
| 6,070,281 A | * | 6/2000 | Reich | A61B 6/04 5/600 |
| 6,094,760 A | * | 8/2000 | Nonaka | A61B 6/0457 5/600 |
| 6,484,332 B2 | * | 11/2002 | Korver, II | A61G 7/1017 5/601 |
| 6,862,762 B1 | * | 3/2005 | Johnson | A61B 6/0442 378/177 |
| 7,847,275 B2 | * | 12/2010 | Lifshitz | A61B 6/032 250/491.1 |
| 7,860,550 B2 | * | 12/2010 | Saracen | A61B 6/0457 378/209 |
| 8,819,877 B2 | * | 9/2014 | Zheng | A61B 6/0457 5/600 |
| 2008/0103391 A1 | * | 5/2008 | Dos Santos Varela | G01T 1/1615 600/436 |
| 2010/0246760 A1 | * | 9/2010 | Li | A61B 6/032 378/37 |
| 2011/0317811 A1 | * | 12/2011 | Scarpellini | A61B 6/0457 378/62 |

FOREIGN PATENT DOCUMENTS

| KR | 10-2010-0005930 A | 1/2010 |
|---|---|---|
| KR | 10-2014-0070749 A | 6/2014 |

* cited by examiner (a)

(b)

(c)

X-RAY TABLE AND X-RAY SYSTEM COMPRISING SAME

CROSS-REFERENCE TO RELATED APPLICATIONS

This application is the National Stage filing under 35 U.S.C. 371 of International Application No. PCT/KR2015/008183, filed on Aug. 5, 2015, which claims the benefit of Korean Patent Application No. 10-2014-0100916, filed on Aug. 6, 2014, Korean Patent Application No. 10-2014-0117235, filed on Sep. 3, 2014, and Korean Patent Application No. 10-2014-0126237, filed on Sep. 22, 2014, the contents of which are all hereby incorporated by reference herein in their entirety.

TECHNICAL FIELD

The present invention relates to an X-ray table for X-ray imaging and an X-ray system including the X-ray table.

BACKGROUND ART

With recent advancement in scientific technology and medical technology, radiation-relevant equipment has been rapidly developed as diagnostic equipment and radiographic equipment has been generalized. An X-ray system is generally known as popularized diagnostic equipment which is radiation-relevant equipment. The X-ray system is used to visualize an anatomical structure and to detect a pathological phenomenon, disease, or an abnormal anatomical structure.

The X-ray system can be roughly classified into a film system, a computed radiography (CR) system, and a digital radiography (DR) system depending on an image acquiring scheme.

The film system is a most general imaging method for X-ray imaging. Here, X-rays passing through a subject form a latent image on a photosensitive film and the photosensitive film is developed by chemical treatment in a darkroom to visualize an image.

The CR system is a method of using an image plate (IP) cassette formed of cumulative fluorescent substance (or photostimulable fluorescent substance) instead of the photosensitive film in the film system. Here, X-rays passing through a subject is left in the form of transformed energy in the IP cassette and is stored as a latent image. Thereafter, when the IP cassette is inserted into an image reader and is irradiated with a laser beam, the IP cassette emits light depending on an amount of X-rays incident on the IP cassette and the image reader converts intensity of emitted light into electrical signals and converts the electrical signals into a digital image.

The DR system is classified into a camera system using a charge-coupled device (CCD) or the like and a panel system. The CCD system uses a CCD sensor and the CCD sensor is partitioned into very small cells which are called pixels. Electric intensity is determined depending on an amount of X-rays incident on each pixel and an electrical signal based thereon is digitalized by an analog-digital converter. The DR system does not need an image reader unlike the CR system and a digital image can be immediately acquired. The panel system includes plural photodetection pixels in a flat panel and each photodetection pixel senses X-rays. Each photodetection pixel senses X-rays which are generated from an X-ray generator and transmitted by a subject and outputs an electrical signal. The electrical signal is read out by a readout integrated circuit (ROIC).

An DR type X-ray system is more expensive than a film type or CR type X-ray system and thus is mainly used in large-scale hospitals and a CR type or film type X-rays system which is relatively cheap is used in small-scale hospitals.

DISCLOSURE OF THE INVENTION

Technical Problem

Therefore, the present invention is made to solve the above-mentioned problem and an object thereof is to provide a digital X-ray table that can reduce installation and maintenance costs and can be conveniently used and an X-ray system including the X-ray table.

Other objects of the present invention have been apparent from the following embodiments.

Solution to Problem

According to an aspect of the present invention, there is provided an X-ray table that is reversibly rotatable without interfering with an X-ray imaging unit while a top surface thereof faces the X-ray imaging unit.

The X-ray table according to the present invention can include one or more of the following features. For example, the X-ray table may rotate into a vertical posture or a horizontal posture.

The X-ray table may further include a top plate and a mobile member that is rotatably coupled to the top plate, and a rotation axis of the mobile member may be located at the center of the top plate or in the vicinity of the center.

The X-ray table may further include a fixed member that is rotatably coupled to the mobile member and the mobile member may overlap the fixed member when the top plate rotates into the vertical posture.

The X-ray table may further include a driving unit that allows the mobile member to rotate.

The mobile member may be rotatably coupled to the top plate by a link.

The X-ray table may further include a mobile member that is rotatably coupled to a top plate.

The X-ray receiver may be coupled to be movable in a length direction of the X-ray table.

The X-ray table may further include a top plate and a part or an overall part of a front surface of the top plate may be opened to expose the X-ray receiver to the outside.

The X-ray receiver may be rotatable about the top plate.

According to another aspect of the present invention, there is provided an X-ray system including the above-mentioned X-ray table.

Advantageous Effects of the Invention

According to the present invention, since independent equipment for vertical imaging does not have to be provided, a single expensive X-ray receiver is used to exhibit an effect based on use of two X-ray receivers. Accordingly, the present invention can provide a digital X-ray table that can reduce installation and maintenance costs and can be conveniently used and an X-ray system including the X-ray table.

DESCRIPTION OF EMBODIMENTS

Figure 1:
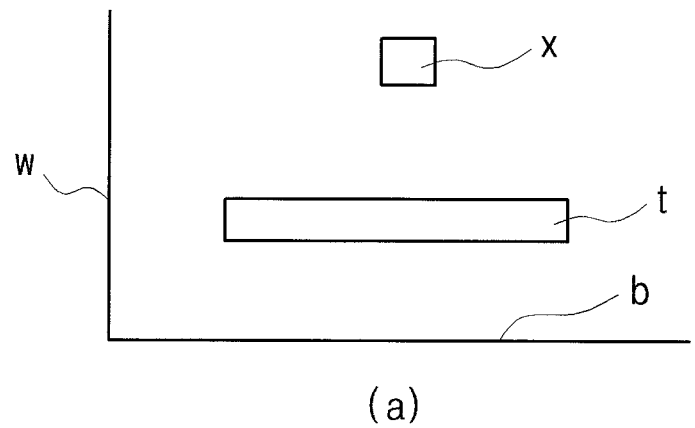
FIG. 1 is a diagram schematically illustrating operation of an X-ray table according to an embodiment of the present invention.
Figure 1:
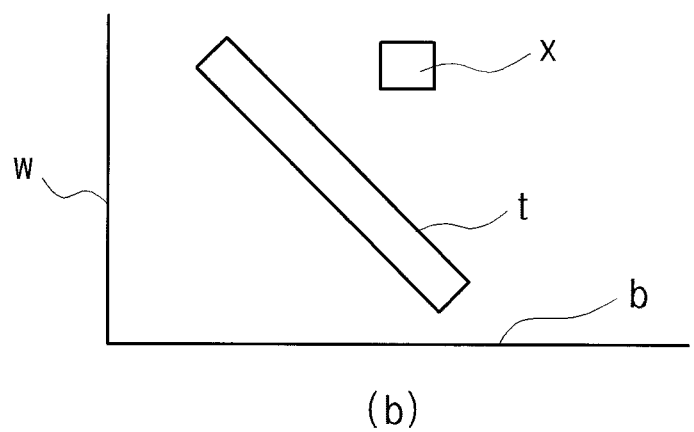
Figure 1:
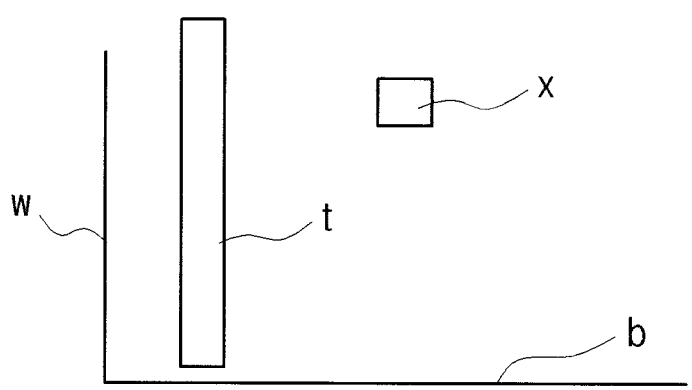

The invention can be modified in various forms and can have various embodiments. Specific embodiments will be illustrated in the drawings and described in detail. However, the embodiments are not intended to limit the invention, but it should be understood that the invention includes all modifications, equivalents, and replacements belonging to the concept and the technical scope of the invention. When it is determined that detailed description of known techniques involved in the invention makes the gist of the invention obscure, the detailed description thereof will not be made.

The terms used in the following description are intended to merely describe specific embodiments, but not intended to limit the invention. An expression of the singular number includes an expression of the plural number, so long as it is clearly read differently. The terms such as "include" and "have" are intended to indicate that features, numbers, steps, operations, elements, components, or combinations thereof used in the following description exist and it should thus be understood that the possibility of existence or addition of one or more other different features, numbers, steps, operations, elements, components, or combinations thereof is not excluded.

Terms such as first and second can be used to describe various elements, but the elements should not be limited to the terms. The terms are used only for distinguishing one element from another element. Terms such as horizontal and vertical should be understood as a concept including cases in which there are some errors as well as mathematical horizontal and vertical.

Hereinafter, embodiments of the invention will be described in detail with reference to the accompanying drawings. In describing the invention with reference to the accompanying drawings, like elements are referenced by like reference numerals or signs regardless of the drawing numbers and description thereof will not be repeated.

FIG. 1 is a diagram illustrating operation of an X-ray table t according to an embodiment of the present invention. In FIG. 1, supports that support the X-ray table t on a floor b are not illustrated.

Referring to FIG. 1, the X-ray table t according to the invention is located below an X-ray imaging unit x and reversibly rotates. The X-ray table rotates without interfering with the X-ray imaging unit x which is fixed in the course of rotation. In the course of rotation, the top surface of the X-ray table t always faces the X-ray imaging unit x.

When the X-ray table t rotates from a horizontal posture illustrated in FIG. 1(a), the X-ray table t horizontally moves to a wall w and is located at a vertical posture illustrated in FIG. 1(c). Referring to FIG. 1(b) corresponding to a rotation course of the X-ray table t, it can be seen that the X-ray table t does not interfere with the X-ray imaging unit x which is located above the X-ray table t.

Accordingly, a subject (not illustrated) lying down in the state illustrated in FIG. 1(a) can be subjected to X-ray imaging and then the subject standing up in the state illustrated in FIG. 1(c) can be subjected to X-ray imaging. The imaging order can be reversed.

X-ray tables t according to embodiments of the present invention will be described below with reference to the accompanying drawings.

First Embodiment

Figure 2:
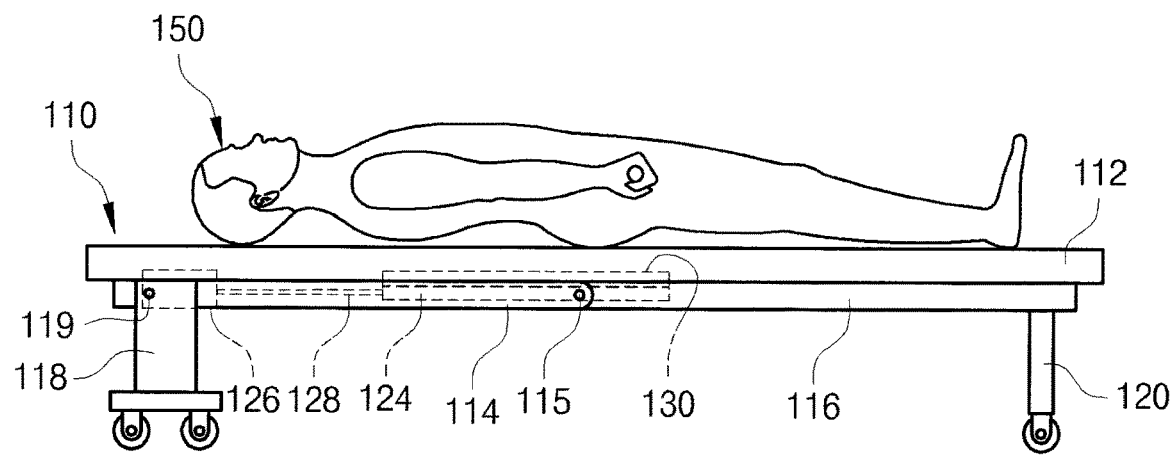
FIG. 2 is a diagram illustrating a state in which an X-ray table according to a first embodiment of the present invention is located horizontal.
Figure 3:
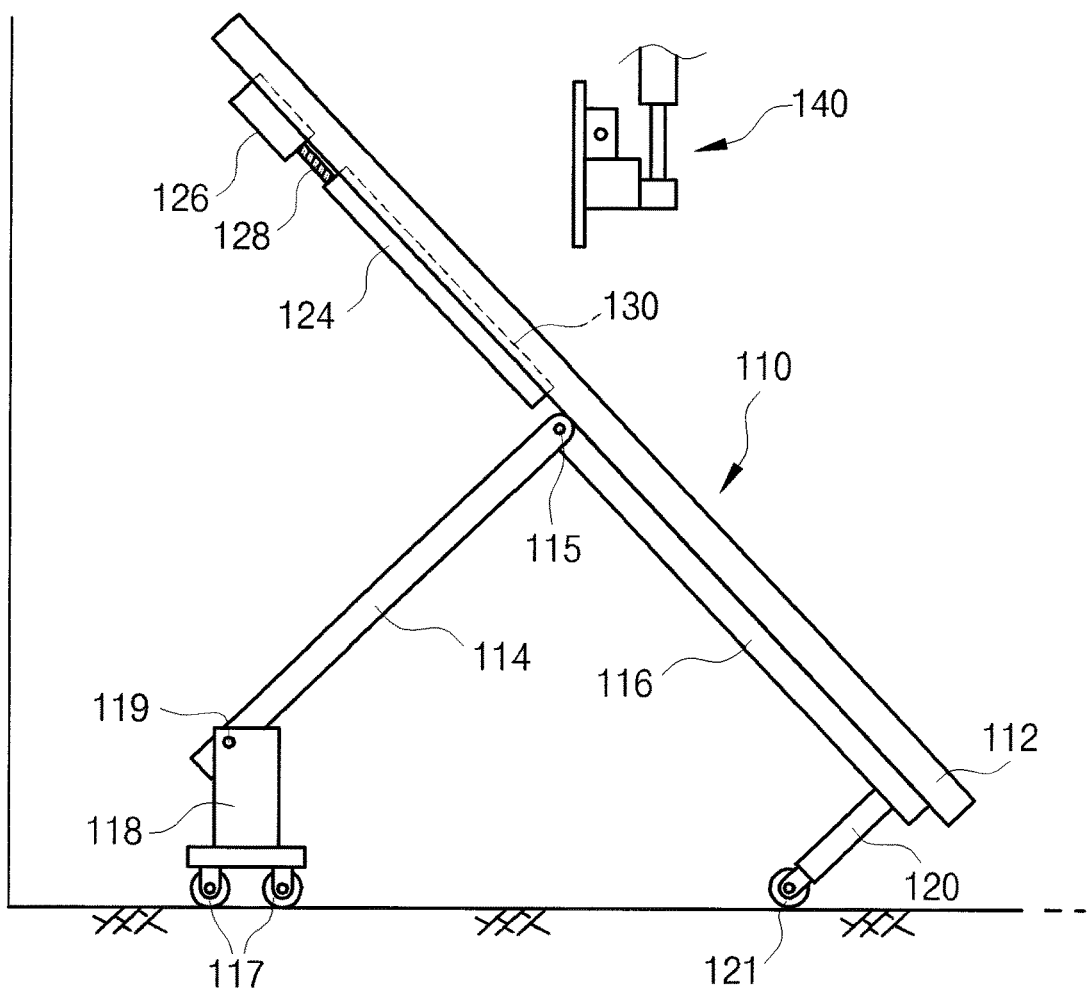
FIG. 3 is a side view illustrating a state in which a top plate rotates with rotation of a mobile member in the X-ray table according to the first embodiment of the present invention.
Figure 4:
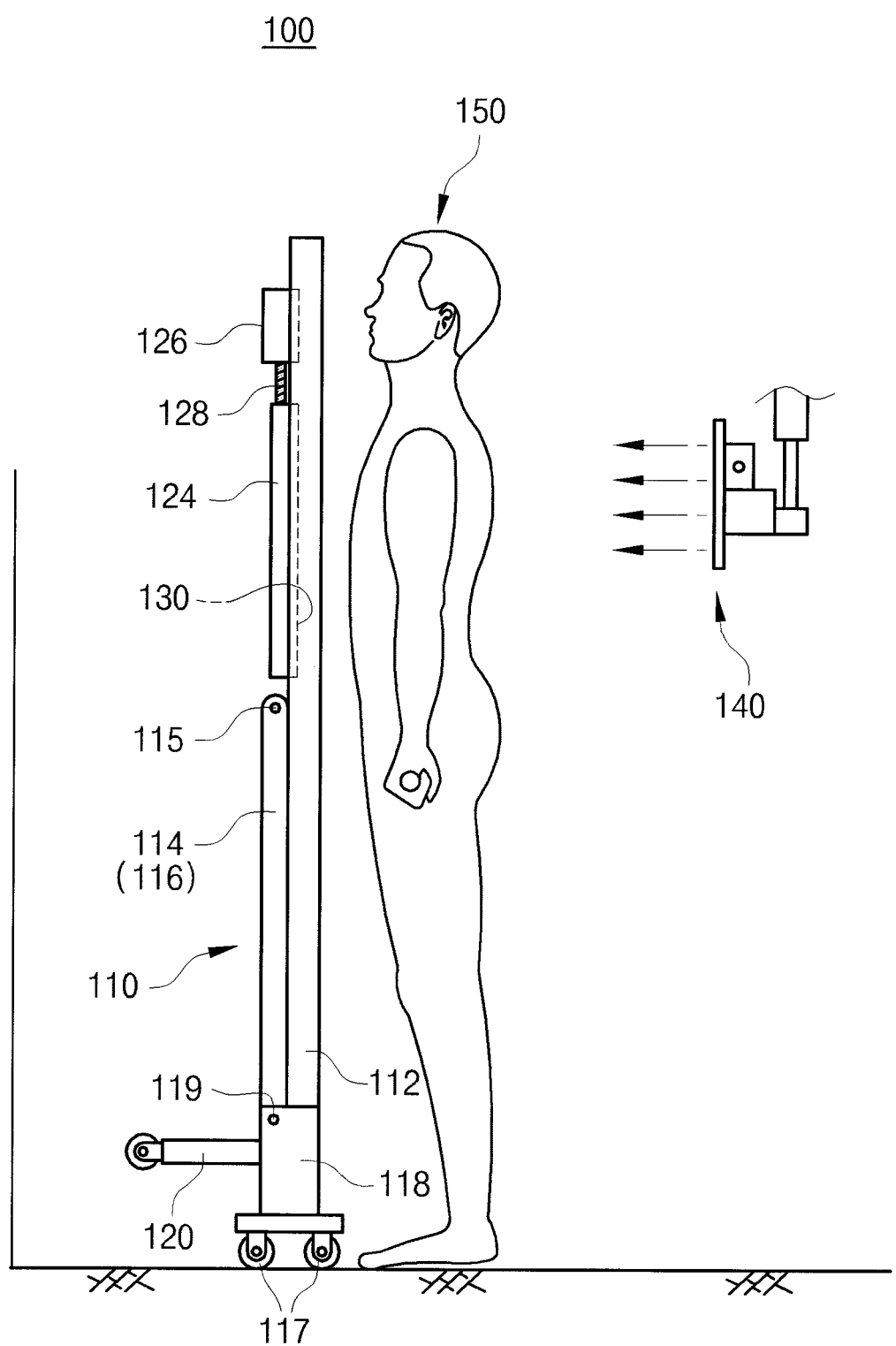
FIG. 4 is a side view illustrating a state in which the X-ray table according to the first embodiment of the present invention is located vertical.
Figure 5:
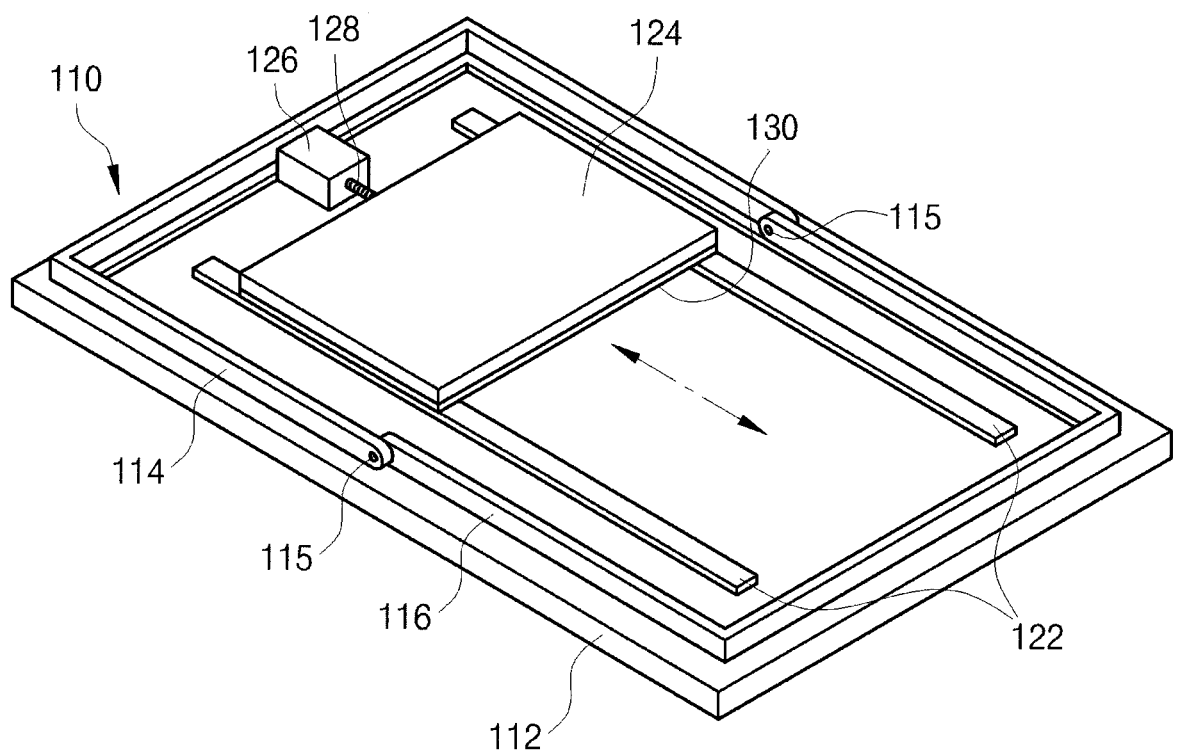
FIG. 5 is a perspective view illustrating a bottom surface of the X-ray table according to the first embodiment of the present invention.

FIG. 2 is a diagram illustrating a state in which an X-ray table 110 according to a first embodiment of the present invention is located in a horizontal posture. FIG. 3 is a side view illustrating a state in which a top plate 112 rotates with rotation of a mobile member 114 in the state illustrated FIG. 2. FIG. 4 is a side view illustrating a state in which the mobile member 114 further rotates in the state illustrated in FIG. 3 such that the top plate 112 is located in a vertical posture. FIG. 5 is a perspective view illustrating a bottom surface of the X-ray table 110 according to the first embodiment of the present invention. A first support 118 and a second support 120 are not illustrated in FIG. 3.

Referring to FIGS. 2 to 5, the X-ray table 110 according to the first embodiment of the present invention is included in an X-ray system 100 and includes an X-ray receiver 130 for X-ray imaging on one surface of the top plate 112. The top plate 112 can be located in the horizontal posture as illustrated in FIG. 2 or the vertical posture as illustrated in FIG. 4. When the top plat e112 is located in the horizontal posture, a subject 150 can lie down thereon and can be subjected to horizontal imaging using X-rays. When the top plate 112 is located in the vertical posture, the subject 150 can stand up in the front thereof and can be subjected to vertical imaging using X-rays. Since the X-ray receiver 130 is movable in the length direction of the top plate 112, the position of the X-ray receiver can be adjusted depending on the horizontal imaging and the vertical imaging.

Since the X-ray table 110 according to this embodiment can allow the horizontal imaging and the vertical imaging on a subject 150, it is not necessary to include an independent imaging stand and an independent X-ray receiver for vertical imaging in the conventional art. Accordingly, since the X-ray system 100 according to this embodiment does not need to include an independent imaging stand and an independent X-ray receiver for vertical imaging, it is possible to reduce installation costs and to facilitate maintenance.

The top plate 112 is located on a mobile member 114 and a fixed member 116 and corresponds to a single plate formed as a unified body. Referring to FIG. 2, when the horizontal imaging using X-rays is performed, a subject 150 can be located on a flat top surface of the top plate 112. Referring to FIG. 4, when the vertical imaging using X-rays is performed, the top plate 112 is located vertically and serves as an imaging stand.

The top plate 112 can be formed of a material (for example, a plastic resin) which can transmit X-rays and which has some hardness. The top plate 112 can be formed of a single member, or may be formed of two members which are rotatably coupled to each other. When the top plate is formed of two members which are rotatably coupled to each other, a particular locking unit (not illustrated) may be used to fix the members.

The top plate 112 is formed with a size enough to allow a subject 150 to lie down thereon.

The top plate 112 can be configured to be movable in a front-rear direction and a right-left direction relative to the mobile member 114 with a four-way structure. The four-way structure is a structure in which the top plate includes rollers or the like, is locked by supply of power such that the top plate 112 does not move, and moves by pushing a switch (such as a foothold). By this four-way structure, only the top plate 112 can move easily without moving a subject 150 to accurately image a desired region with X-rays.

Various structures other than the four-way structure can be used as the structure for allowing the top plate 112 to move.

The mobile member 114, the fixed member 116, and the X-ray receiver 130 are located on one surface (for example, a bottom surface) of the top plate 112.

The mobile member 114 has a fallen "U" shape and is located on one surface of the top plate 112. An end of the mobile member 114 is rotatably coupled to the fixed member 116.

The fixed member 116 is a fallen "U" shape and is coupled to one surface of the top plate 112 to be symmetric to the mobile member 114. The mobile member 114 is rotatably coupled to an end of the fixed member 116 by a rotary hinge 115. The rotary hinge 115 can be disposed at the center in the length direction of the top plate 112 or in the vicinity of the center.

When the top plate 112 is located in the horizontal posture as illustrated in FIG. 2, the mobile member 114 is also located in the horizontal posture and comes in contact with the one surface of the top plate 112. The mobile member 114 can be separated and rotated from the top plate 112 such that the top plate 112 is located in the vertical posture as illustrated in FIG. 4. The mobile member 114 separated from the top plate 112 rotates in one direction (a counterclockwise direction in FIG. 3) and overlaps the fixed member 116 in the vertical posture as illustrated in FIG. 4.

In this way, by causing the mobile member 114 to rotate relative to the fixed member 116, the top plate 112 can be located in the horizontal posture as illustrated in FIG. 2 or the vertical posture as illustrated in FIG. 4. The top plate 112 may be located in a tilted posture depending on the degree of rotation of the mobile member 114.

Referring to FIGS. 3 and 4, the top surface of the top plate 112 always face an X-ray imaging unit 140 in the course of rotating. In the course of rotating, the top plate 112 does not interfere with the X-ray imaging unit 140 which is located above the top plate. When the top plate 112 rotates to the vertical posture as illustrated in FIG. 4, the top plate 112 is located in the vicinity of the wall w.

One end of the mobile member 114 is provided with a first support 118. The first support 118 causes the mobile member 114 to have a constant height from the floor. The first support 118 is rotatably coupled to the mobile member 114 by a rotary hinge 119.

A second support 120 is coupled to an end of the fixed member 116. The second support 120 causes the fixed member 116 to have a constant height from the floor.

The first support 118 and the second support 120 include casters 117 and 121 and thus are movable relative to the floor. The first support 118 may be rotatably coupled to one spot of the floor and the second support 120 may be freely separated from the floor. The second support 120 may be rotatably coupled to the top plate 110 and the second support 120 may be brought into close contact with the top plate 110 when the top plate 110 is located in the vertical posture.

The mobile member 114 and the fixed member 116 have the same height. The mobile member 114 has a width slightly larger than that of the fixed member 116. Accordingly, when the mobile member 114 rotates and the top plate is located in the vertical posture as illustrated in FIG. 4, the mobile member 114 and the fixed member 116 completely overlap each other, whereby the total thickness which is the total sum of the thicknesses of the top plate 112 and the fixed member 116 does not increase.

In the X-ray table 110 according to this embodiment, the mobile member 114 and the fixed member 116 have a fallen "U" shape and are arranged symmetrical to each other, but this configuration is only an example and the present invention is not limited by the shapes of the mobile member and the fixed member. The mobile member and/or the fixed member may have various shapes such as a plate shape or a rod shape other than the fallen "U" shape. The X-ray table according to the present invention may not include the fixed member. For example, an independent fixing member may not be provided by rotatably coupling the fixed member 116 to a bottom surface or a side surface of the top plate 112.

The X-ray receiver 130 receives X-rays which are generated from the X-ray imaging unit 140 and which passes through a subject 150, and converts the received X-rays into an electrical signal proportional to the intensity of the X-rays to enable real-time diagnosis.

A single X-ray receiver 130 is disposed on one surface of the top plate 112. The X-ray table 110 according to this embodiment can perform the vertical imaging as well as the horizontal imaging by causing the top plate 112 to rotate, and thus does not need to include two or more X-ray receivers 130. Accordingly, it is possible to reduce initial installation costs of the X-ray system and to reduce maintenance costs.

The X-ray receiver 130 is coupled to one surface of the top plate 112 to be movable in the length direction thereof. The X-ray table 110 according to this embodiment includes guide rails 122, a stage 124, an actuator 126, and a connecting rod 128 for the purpose of linear reciprocation of the X-ray receiver 130.

A pair of guide rails 122 is disposed in parallel on one surface of the top plate 112 and serves to guide the stage 124 to linearly reciprocate. The stage 124 is guided by the guide rails 122 and reciprocates linearly in the length direction of the top plate 112. The guide rails 122 and the stage 124 are generally known and thus specific description thereof will not be made.

The X-ray receiver 130 is fixed onto the stage 124 and thus the X-ray receiver 130 can reciprocate linearly in the length direction of the top plate 112 along with the stage 124. Accordingly, when the horizontal imaging (see FIG. 2) and the vertical imaging (see FIG. 4) are performed, the X-ray receiver 130 can be located at optimal positions for performing X-ray imaging of a subject 150.

The actuator 126 provides a driving force for causing the stage 124 to reciprocate linearly and the driving force output from the actuator 126 is transmitted to the stage 124 via the connecting rode 128. The actuator 126 may be a ball screw or a linear motor, and the present invention is not limited by the actuator 126 for driving the stage 124.

The X-ray receiver 130 may not include the independent stage 124 but may be directly driven by the actuator 126. An X-ray table according to another embodiment may not include an independent actuator but a user may directly drive the X-ray receiver 130.

Use of the X-ray table 110 according to the first embodiment will be described below with reference to FIGS. 2 to 5.

FIG. 2 illustrates an example in which a subject 150 is subjected to the horizontal imaging. In the horizontal imaging, a waist, a pelvis, or the like of the subject 150 can be imaged with X-rays. In case of the horizontal imaging, the mobile member 114 does not rotate and comes in close contact with one surface of the top plate 112 and thus the top plate 112 is disposed horizontal or almost horizontal. In case of the horizontal imaging, the X-ray receiver 130 is located in an imaging region (for example, a waist or a pelvis) of the subject 150. When setting of the X-ray table 110 is completed, the imaging unit (which is denoted by reference numeral 140 in FIG. 4) moves just above the imaging region and then performs the X-ray imaging.

When the horizontal imaging is difficult or the vertical imaging is more effective, the top plate 112 is made to stand vertically or almost vertically to perform the vertical imaging as illustrated in FIG. 4. For the vertical imaging, the top plate 112 should be made to stand vertically as illustrated in FIG. 4. The mobile member 114 rotates in one direction (the counterclockwise direction in FIG. 3) to completely overlap the fixed member 116 as illustrated in FIG. 4. Accordingly, the mobile member 114 comes in close contact with another part of the bottom surface of the top plate 112.

In the course of causing the top plate 112 to rotate from the horizontal posture to the vertical posture, the top surface of the top plate 112 does not interfere with the X-ray imaging unit 140 while always facing the X-ray imaging unit 140.

When the top plate 112 is located in the vertical posture as illustrated in FIG. 4, the top plate 112 is disposed adjacent to the wall w. When the top plate 112 is located in the vertical posture, a subject 150 stands in front of the top plate 112 for the X-ray imaging. The top plate 112 can be maintained in the vertical posture by a locking unit (not illustrated) included in the first support 118.

Referring to FIG. 4, the X-ray system 100 according to the present invention includes the X-ray table 110 including the X-ray receiver 130 and the X-ray imaging unit 140. Since the X-ray imaging unit 140 can adjust the position thereof and an X-ray irradiation direction, it is possible to easily cope with the horizontal imaging and the vertical imaging. The X-ray system 100 according to the present invention may include a monitor (not illustrated) for displaying an imaging result in addition to the X-ray table 110 and the X-ray imaging unit 140.

Second Embodiment

Hereinafter, an X-ray table 210 according to a second embodiment of the present invention will be described with reference to FIG. 6. The X-ray table 210 has a configuration similar to the configuration of the X-ray table 110 according to the first embodiment and thus description of the same configuration will not be repeated.

Figure 6:
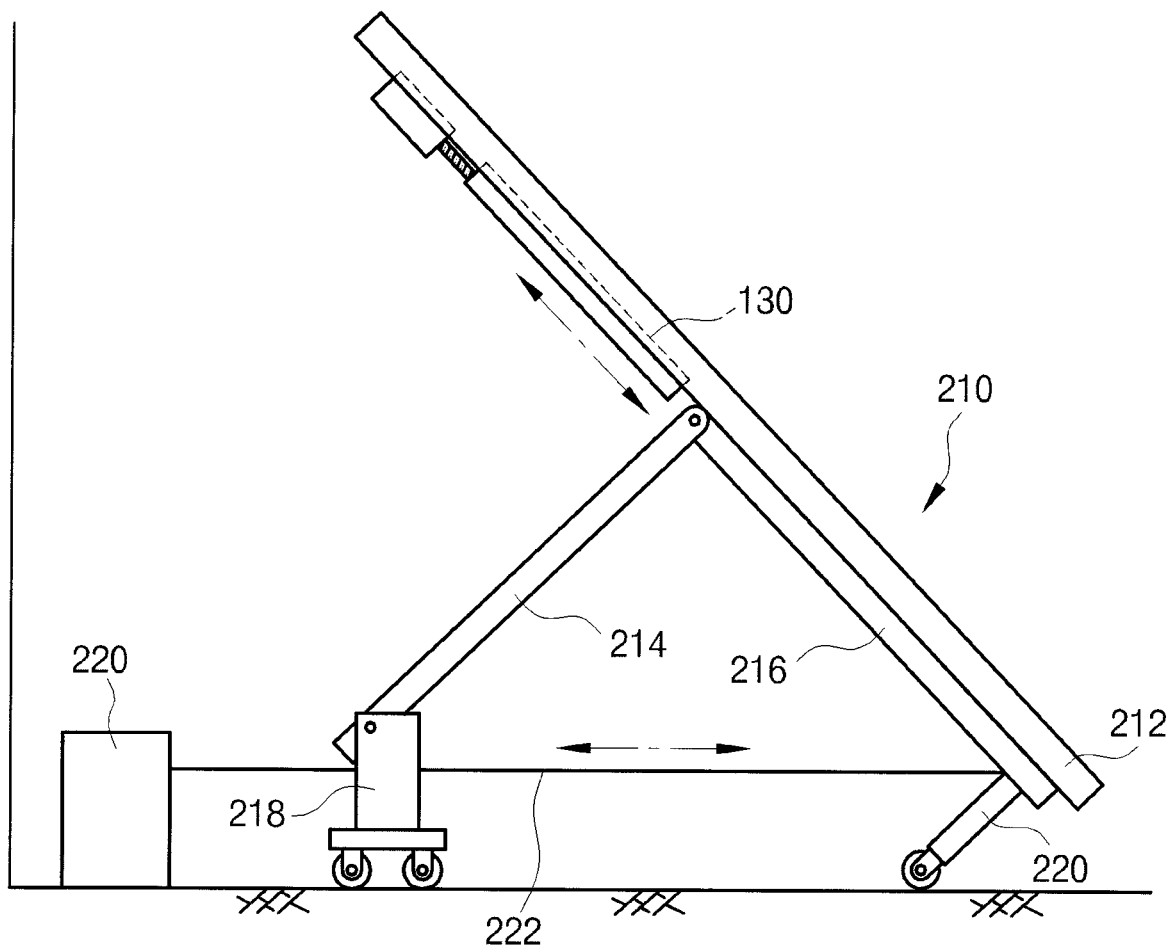
FIG. 6 is a side view illustrating an X-ray table according to a second embodiment of the present invention.

FIG. 6 is a side view illustrating the X-ray table 210 according to the second embodiment.

The X-ray table 210 according to the second embodiment includes a driving unit 220 that causes a mobile member 214 of the X-ray table 210 to rotate and causes a top table 212 to stand vertically. The driving unit 220 is connected to a fixed member 216 corresponding to the other end of the top table 212 by a wire 222. One end of the mobile member 214 is rotatably coupled to the floor by a first support 218, and the other end of the fixed member 216 is configured to be movable relative to the floor by a second support 220.

When the driving unit 220 is activated to draw the wire 222, the mobile member 214 in close contact with one surface of the top table 212 rotates in one direction (the counterclockwise direction in FIG. 6) to overlap the fixed member 216. Accordingly, the top table 212 is disposed vertical or almost vertical.

The X-ray table 210 according to the second embodiment causes the mobile member 214 to rotate using the wire 222, but the present invention is not limited by the unit for causing the mobile member 214 to rotate. Accordingly, the X-ray table 210 according to the second embodiment can use a hydraulic cylinder, a pneumatic cylinder, or a motor to cause the mobile member 214 to rotate.

Third Embodiment

Hereinafter, an X-ray table 310 according to a third embodiment of the present invention will be described with reference to FIG. 7.

Figure 7:
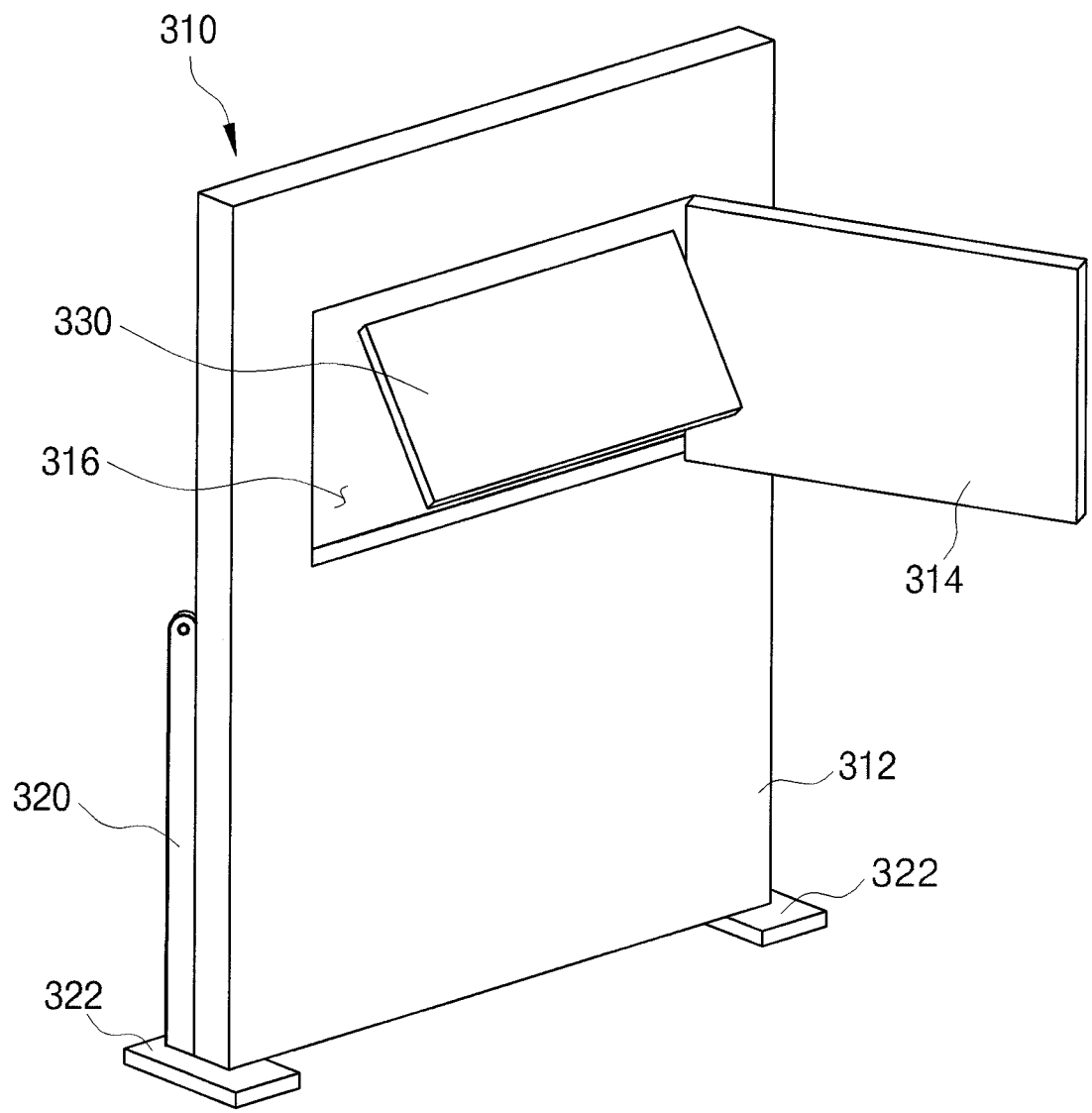
FIG. 7 is a perspective view illustrating an X-ray table according to a third embodiment of the present invention.

FIG. 7 is a perspective view illustrating the X-ray table 310 according to the third embodiment of the present invention.

Referring to FIG. 7, the X-ray table 310 according to this embodiment has a configuration similar to the configuration of the X-ray table 110 according to the first embodiment, except that a part of a front surface of a top plate 312 is opened to expose an X-ray receiver 330. The X-ray receiver 330 is configured to be rotatable relative to the top plate 312 by a predetermined angle.

A window 314 is rotatably disposed on the front surface of the top plate 312. When the window 314 is opened, an accommodation groove 316 and the X-ray receiver 330 accommodated in the accommodation groove 316 is exposed to the outside. The X-ray receiver 330 is rotatably coupled to the accommodation groove 316.

The X-ray table 310 according to this embodiment is opened by rotation of the window 314, but the window can open the accommodation groove 316 using a sliding door structure.

The X-ray receiver 330 is exposed to the outside when the window 314 is opened, whereby a subject can be brought into close contact with the X-ray receiver 330 for imaging and maintenance of the X-ray receiver 330 is facilitated. The X-ray receiver 330 is rotatable, whereby a subject's specific region (for example, a head or a chest) can be brought into close contact with the X-ray receiver for the X-ray imaging.

A mobile member 320 is rotatably coupled to one surface of the top plate 312 and is the same as the mobile member 114 in the first embodiment and thus specific description thereof will not be repeated. A base 322 is disposed at one end of the mobile member 320. The base 322 may be selectively fixed to the floor to be movable if necessary.

A part of the front surface of the top plate 312 of the X-ray table 310 according to this embodiment is opened, but the entire front surface of the top plate 312 may be opened.

Fourth Embodiment

Hereinafter, an X-ray table 410 according to a fourth embodiment of the present invention will be described with reference to FIGS. 8 to 10.

Figure 8:
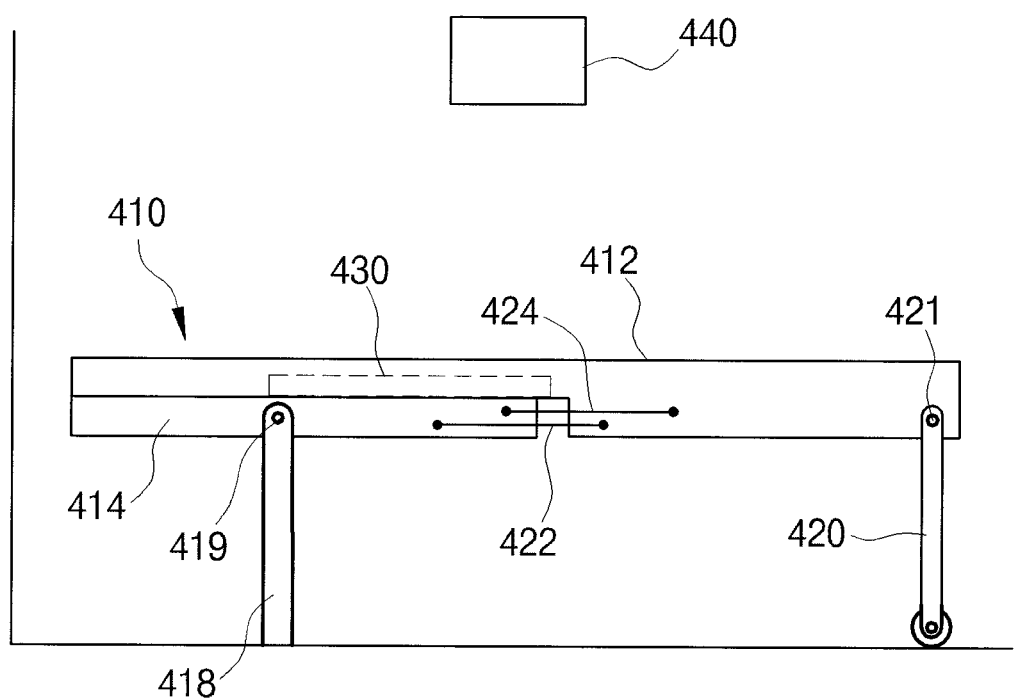
FIGS. 8 to 10 are diagrams illustrating an X-ray table according to a fourth embodiment of the present invention.
Figure 9:
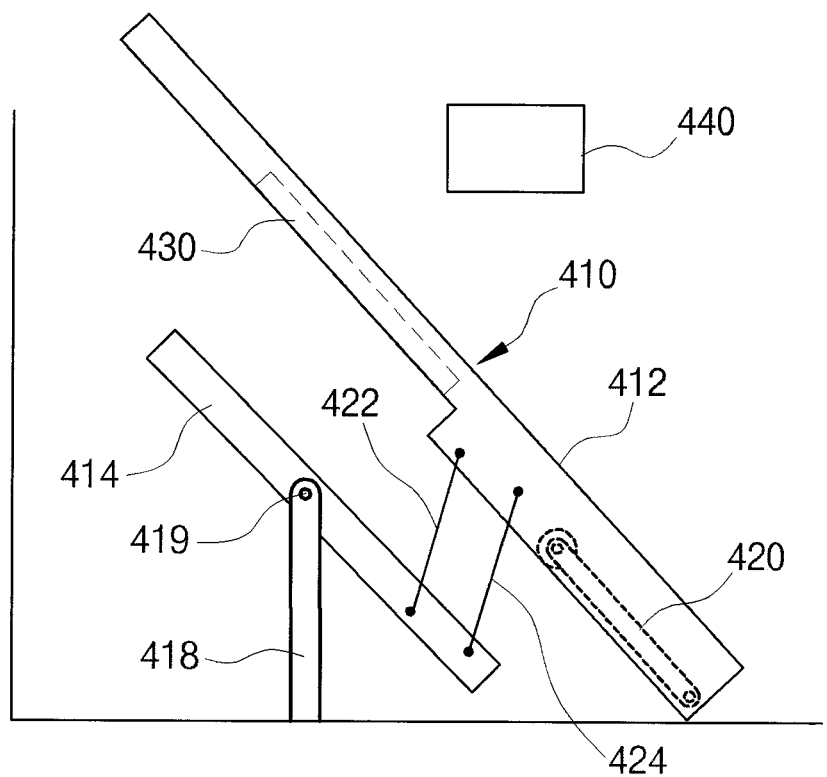
Figure 10:
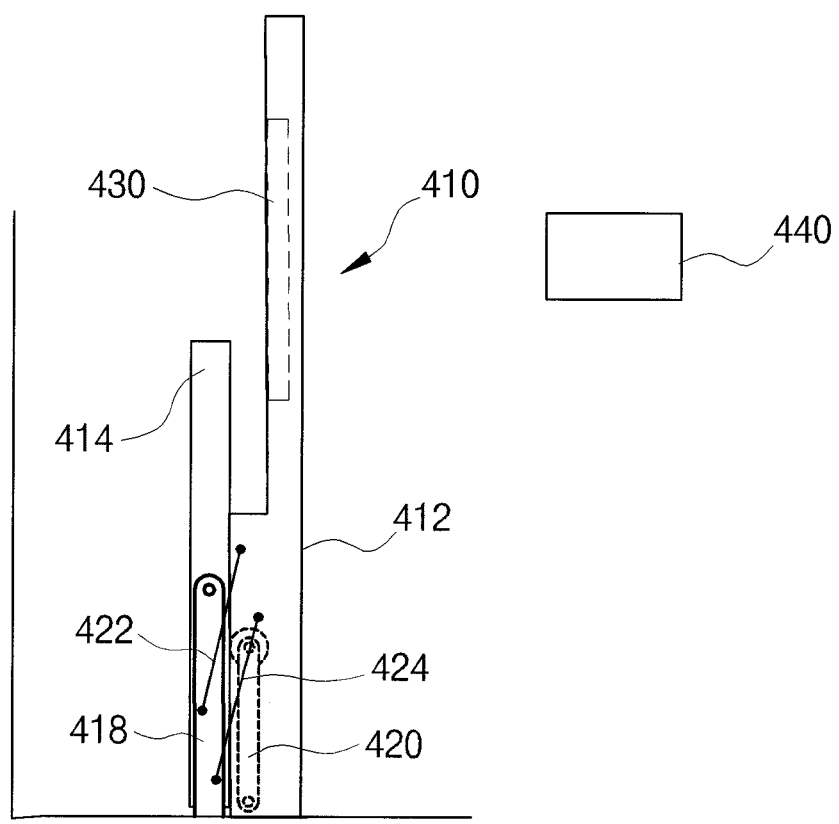

FIGS. 8 to 10 are side views illustrating the X-ray table 410 according to the fourth embodiment of the present invention and sequentially illustrate the course of causing the X-ray table 410 to rotate along with the rotation of a mobile member 414 from the horizontal posture to the vertical posture.

The X-ray table 410 according to this embodiment has a configuration similar to that of the X-ray table 110 according to the first embodiment, except that a top plate 412 and the fixed member (see reference numeral 116 in FIG. 3) are formed as a unified body or an independent fixed member is not provided and the rotation directions of the mobile member 414 and the top plate 412 are the same. That is, when the mobile member 414 rotates in one direction (the clockwise direction in FIGS. 8 to 10) in the horizontal posture, the top plate 412 also rotates in the same direction and thus the top plate 412 has a desired angle (a horizontal state, a vertical state, or a tilted state).

The X-ray table 410 according to this embodiment includes a top plate 412, a mobile member 414 that is rotatably coupled to the top plate 412 by first and second links 422 and 424, and an X-ray receiver 430 that is coupled to the top plate 412 to be linearly movable. A second support 420 is rotatably coupled to the top plate 412, and a first support 418 is rotatably coupled to the mobile member 414.

The top plate 412 is similar to the top plate 112 according to the first embodiment and thus specific description thereof will not be repeated. The top plate 412 according to this embodiment does not include a fixed member (see reference numeral 116 in FIG. 3) and rotates in the same direction while maintaining a constant positional relationship with the mobile member 414 by the first and second links 422 and 424.

Ends of the first link 422 and the second link 424 are rotatably coupled to right and left side surfaces of the top plate 412 and the mobile member 414. The first link 422 and the second link 424 have constant rigidity and thus do not have a variation in length. Accordingly, the top plate 412 and the mobile member 414 rotate in the same direction with a constant gap by the first link 422 and the second link 424.

The X-ray table 410 according to this embodiment includes two rigid links 422 and 424, but this configuration is exemplary and the present invention is not limited by the number of links, the positions, and the characteristics. For example, one or three or more links may be provided and the link may have flexibility.

The mobile member 414 rotates manually by a user or automatically by a driving unit (not illustrated, such as a motor) and is rotatably coupled to the top plate 412. The mobile member 414 according to this embodiment is the same as the X-ray table 110 according to the first embodiment, except for the rotation direction based on the first and second links 422 and 424.

Referring to FIG. 8, when the top plate 412 is located in the horizontal posture, the mobile member 414 is also located in the horizontal posture and comes in close contact with the bottom surface of the top plate 412. The top plate 412 is located below an X-ray imaging unit 440 with a predetermined gap therebetween.

Referring to FIG. 9, when the mobile member 414 rotates in one direction (the clockwise direction in FIG. 9) by a user's manual operation or by a driving unit (not illustrated) such as a motor, the top plate 412 is separated from the mobile member 414 by a constant gap and rotates in the same direction by the first link 422 and the second link 424 (see FIG. 9). At this time, the second support 420 rotatably coupled to the top plate 412 can rotate to come in contact with the top plate 412. The top plate 412 rotates without interfering with the X-ray imaging unit 440. In the course of rotation of the top plate 412, the top surface thereof always faces the X-ray imaging unit 440.

Referring to FIG. 10, when the mobile member 414 rotates to the vertical posture, the top plate 412 is also located in the vertical posture by the first link 422 and the second link 424 and the mobile member 414 can come in close contact with the bottom surface of the top plate 412. At this time, the top plate 412 is located adjacent to the wall.

The mobile member 414 may have a plate shape or may have various shapes other than the plate shape like the mobile member 114 according to the first embodiment. A first support 418 is rotatably coupled to the mobile member 414 by a rotary hinge 419. The lower end of the first support 418 may be fixed to or movable relative to the floor.

A second support 420 is rotatably coupled to the top plate 412 and has the same height as the first support 418. When the top plate 412 is located in the vertical posture as illustrated in FIG. 10, the second support 420 may be maintained in a folded state or may be folded and located in the top plate 412 (which is indicated by a dotted line 420 in FIG. 10).

The X-ray receiver 430 (indicated by a dotted line) is coupled to the top plate 412 to be movable in the length direction thereof.

While embodiments of the present invention have been described above, those skilled in the art can understand that the invention can be modified and changed in various forms without departing from the concept and scope of the invention described in the appended claims.

The invention claimed is:

1. An X-ray table that is reversibly rotatable without interfering with an X-ray imaging unit while a top surface thereof faces the X-ray imaging unit, the X-ray table comprising:
    a top plate;
    an X-ray receiver provided on a bottom surface of the top plate for receiving X-rays such that the X-ray receiver rotates together with the top plate;
    a fixed member fixed to the bottom surface of the top plate; and
    a mobile member having a first end rotatably coupled to the fixed member and a second end rotatably coupled to a first support moveable on a floor such that when the mobile member rotates in a direction, the top plate rotates in an opposite direction.

2. The X-ray table according to claim 1, wherein the top plate rotates between a horizontal position and a vertical direction.

3. The X-ray table according to claim 1,
    wherein a rotation axis of the mobile member is located at a center of the top plate or in the vicinity of the center.

4. The X-ray table according to claim 1,
    wherein when the top plate is in a vertical position, the mobile member completely overlaps the fixed member.

5. The X-ray table according to claim 1, further comprising a driving unit that allows the mobile member to rotate.

6. The X-ray table according to claim 1, wherein the X-ray receiver is movable in a length direction of the top plate.

7. The X-ray table according to claim 1,
    wherein a part or an overall part of a front surface of the top plate is opened to expose the X-ray receiver to the outside.

8. The X-ray table according to claim 7, wherein the X-ray receiver is rotatable about the top plate.

9. The X-ray table according to claim 1, wherein an entire portion of the mobile member is in contact with the top plate when the top plate is in a horizontal position.

10. The X-ray table according to claim 1, wherein the mobile member and the fixed member have a U shape.

11. A rotatable X-ray table comprising:
a top plate;
an X-ray receiver provided on a bottom surface of the top plate for receiving X-rays such that the X-ray receiver rotates together with the top plate;
a mobile member rotatably coupled to a first support fixed to a floor; and
a plurality of rigid links rotatably coupled between the top plate and the mobile member such that when the mobile member rotates in a direction, the top plate rotates in a same direction, wherein the X-ray receiver is rotatably coupled to the top plate.

12. The rotatable X-ray table according to claim 11, wherein the mobile member is positioned in a recess area of the top plate and is in contact with the top plate when the top plate is in a horizontal position.

13. The rotatable X-ray table according to claim 11, wherein the X-ray receiver is moveable in a length direction of the top plate.

14. The rotatable X-ray table according to claim 11, wherein a part of a front surface of the top plate is opened to expose the X-ray receiver.

15. The rotatable X-ray table according to claim 11, wherein an end of the top plate is rotatably coupled to a second support which supports the top plate when the top plate is in a horizontal position.

16. A rotatable X-ray table comprising:
a top plate;
an X-ray receiver provided on a bottom surface of the top plate for receiving X-rays such that the X-ray receiver rotates together with the top plate;
a mobile member rotatably coupled to a first support fixed to a floor; and
a plurality of rigid links rotatably coupled between the top plate and the mobile member such that when the mobile member rotates in a direction, the top plate rotates in a same direction, wherein the mobile member is positioned in a recess area of the top plate and is in contact with the top plate when the top plate is in a horizontal position.

* * * * *